United States Patent [19]

Mansat et al.

[11] Patent Number: 5,108,431
[45] Date of Patent: Apr. 28, 1992

[54] LIGAMENT ANCHOR

[75] Inventors: Christian Mansat, Balma, France; Otto Frey, Winterthur; Roland Willi, Stadel, both of Switzerland

[73] Assignees: Sulzer Brothers Limited, Winterthur; Protek AG, Berne, both of Switzerland

[21] Appl. No.: 724,157

[22] Filed: Jul. 1, 1991

[30] Foreign Application Priority Data

Jul. 6, 1990 [CH] Switzerland ............ 02242/90

[51] Int. Cl.⁵ ............................................. A61F 2/08
[52] U.S. Cl. ............................................. 623/13
[58] Field of Search ............................................. 623/13

[56] References Cited

U.S. PATENT DOCUMENTS 4,870,957 10/1989 Goble et al. .................. 623/13

FOREIGN PATENT DOCUMENTS 0232049 8/1987 European Pat. Off. .
0342281 11/1989 European Pat. Off. .
89143086 5/1990 Fed. Rep. of Germany .
2395012 1/1979 France .
2586927 3/1987 France .

Primary Examiner—David Isabella
Assistant Examiner—Debra S. Brittingham
Attorney, Agent, or Firm—Kenyon & Kenyon

[57] ABSTRACT

The ligament anchor is used for fastening an artificial ligament in a bone. The ligament anchor is formed of a clamp sleeve which tapers on the outside and is deformable radially to a smaller inner diameter. The clamp sleeve has projecting saw tooth segments on the inside with steep flanks against the direction of loading for engaging in the inserted ligament. The clamp sleeve is supported by an anchoring sleeve which tapers internally and is inserted in the opening of the bone. For anchoring, the ligament is pulled outwards under pressure against the direction of loading and the clamp sleeve is pressed into the anchoring sleeve in the direction of loading until the saw tooth elements embrace and hold the ligament such that under the built-up pressure and the ligament tension in the direction of loading, self locking of the sleeves take place.

11 Claims, 2 Drawing Sheets

LIGAMENT ANCHOR

This invention relates to a ligament anchor. More particularly, this invention relates to a ligament anchor for fastening an artificial ligament in a bone.

Heretofore, various types of artificial tendons and ligaments have been known, for example, from Swiss Patent, 644,748 and published European Patent Application 0067929. Generally, after such artificial ligaments have been pulled through an opening in bone tissue, the ligaments have been fixed to the outer surface of the bone by staples. However, the use of staples may result in damage or excessive peak tensions arising in the inserted ligament which may restrict the long term function of the ligament.

Other types of securing devices for securing a ligament to a bone have also been known. For example, French patent 2,395,012 describes the use of a conical plug-like element which is to be inserted into an opening of a bone and through which a ligament end is passed as well as a cross-pin which passes through a loop in the end of the ligament in order to hold the ligament in place while effecting a tension force in the ligament. However, the achievement of an appropriate length of ligament in this situation demands extensive preparation and great skill. Other types of anchoring devices have always been known, for example, from French Patent 2,586,927 wherein use is made of a clamp-like structure wherein a plug fits into a sleeve to clamp extended ends of a ligament therebetween. Similar types of clamping arrangements have always been known from published European Patent Application 0232049 and 0342281. Still other types of structures have been known from German Gebrauchsmuster G8914308.6 which employ a hollow sleeve and one or two toothed segments within the sleeve for gripping a ligament passing therethrough. However, such a construction requires manipulation of the various components in order to achieve anchorage and it produces stress peaks in the ligament.

Accordingly, it is an object of the invention to simplify the anchoring of a ligament in a bone and to provide equal clamping forces over the clamping length.

It is another object of the invention to provide a ligament anchor of relatively simple construction which can be readily manipulated by a surgeon during implantation of a ligament.

Briefly, the invention provides a ligament anchor for fastening an artificial ligament in a bone which is comprised of two elements, namely an anchoring sleeve and a radially deformable clamp sleeve.

The anchoring sleeve is constructed for insertion in a bone opening and has a conical inner surface defining a bore extending therethrough.

The radially deformable clamp sleeve is sized for insertion within the bore within the anchoring sleeve and has a conical outer surface for frictionally engaging with the inner surface of the anchoring sleeve. The clamp sleeve also has a plurality of inwardly facing sawtoothed segments for engaging with a ligament passing through the clamp sleeve. Each of these segments has a plurality of teeth for engaging in a received ligament with each tooth having a steep flank directed towards an enlarged end of the clamp sleeve.

In use, the anchoring sleeve can be first implanted in a bone opening with the ligament then being threaded through the anchoring sleeve. Thereafter, the radially deformable clamp sleeve is placed over the ligament and, while the ligament is held in tension, the clamp sleeve can be slid along the ligament into the anchoring sleeve so as to be deformed radially to a smaller inner diameter while the teeth of the sawed tooth segments penetrate into the ligament. The steep flanks of the teeth of the segments, in this respect, are directed against the direction of loading so as to enhance the gripping of the ligament by the clamp sleeve.

The advantages of the ligament anchor are to be seen in that, upon placing and possibly after tensioning the artificial ligament does not involve risks of any kind which may make an exchange of the ligament necessary due to damage or due to an inappropriate length.

These and other objects and advantages of the invention will become more apparent from the following detailed description taken in conjunction with the accompanying drawings wherein.

Figure 1:
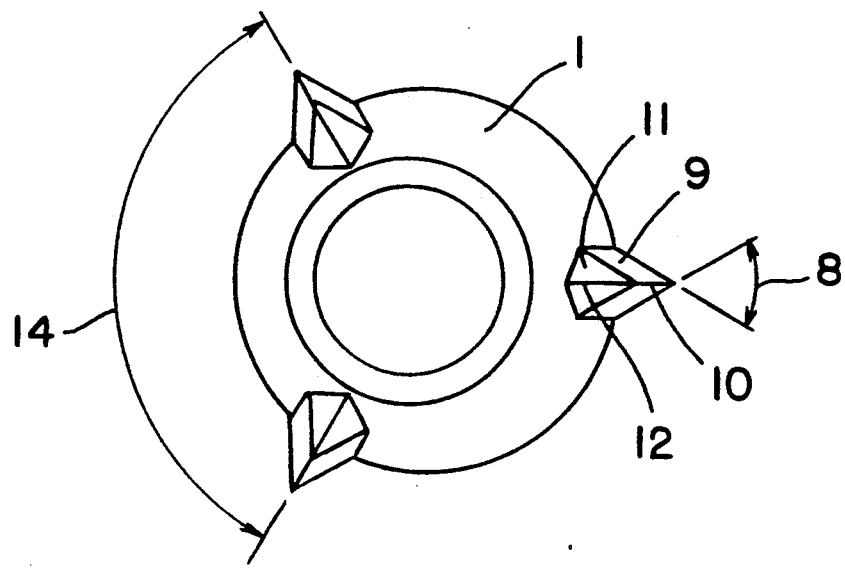
FIG. 1 illustrates an end view of an anchoring sleeve constructed in accordance with the invention.
Figure 6:
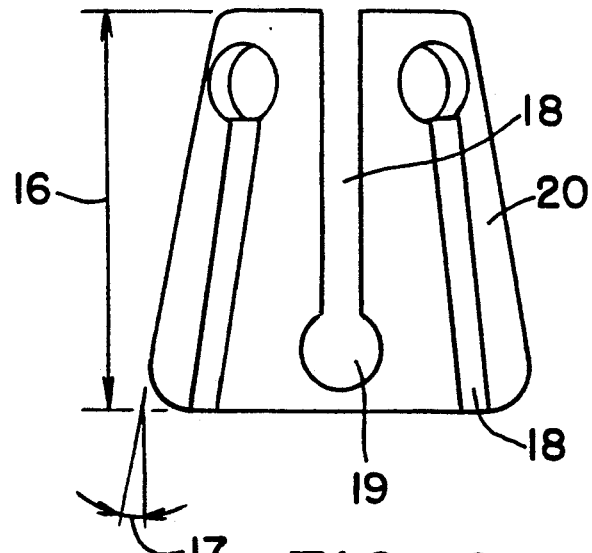
FIG. 6 illustrates a side view of the clamps sleeve of FIGS. 3 and 4.

Referring to FIGS. 1 and 6, the ligament anchor for fastening an artificial ligament in a bone is formed of an anchoring sleeve 1 and a radially deformable clamp sleeve 20.

Figure 2:
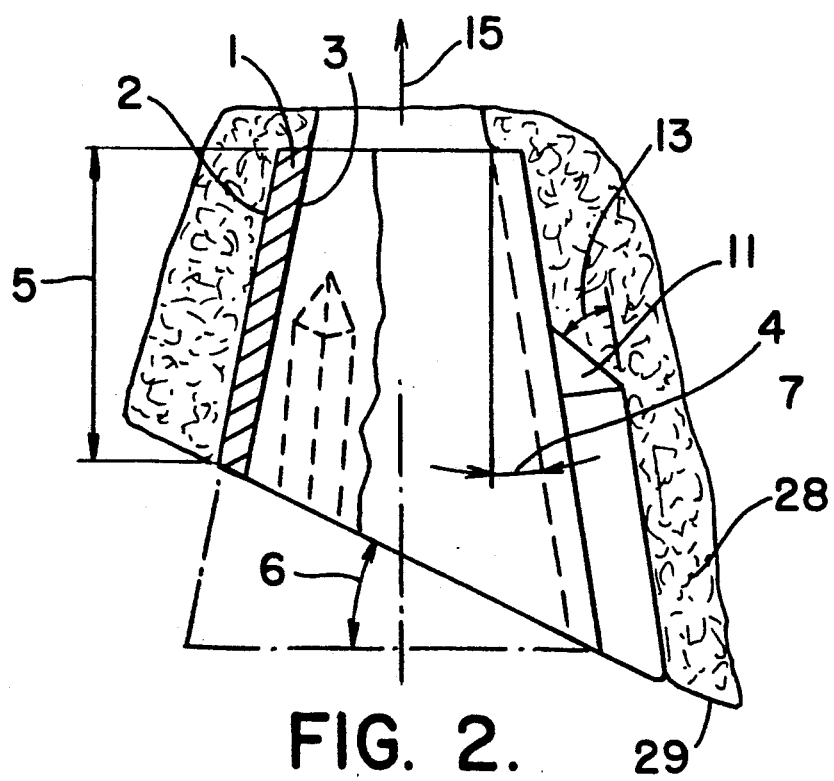
FIG. 2 illustrates a part cross-sectional view of the anchoring sleeve within the bone opening.

Referring to FIGS. 1 and 2, the anchoring sleeve 1 is sized for insertion in an opening of a bone 28 through which an artificial ligament is to be passed. As indicated, the anchoring sleeve 1 has a conical outer surface 2 which tapers inwardly in a first direction as indicated by the arrow 15 and a conical inner surface 3 which defines a longitudinal bore. In this respect, the opening in the bone 28 is typically formed with a conical taper in the direction indicated by the arrow 15 which is the direction of loading of the ligament which is to pass through the opening. The conical surfaces 2, 3 of the anchoring sleeve 1 are each disposed on an angle of taper 4 (i.e. the half-apex angle) of the order of magnitude of 10°. Further, the anchoring sleeve 1 has an enlarged end with a bevel 6 such that the sleeve 1 terminates at the surface 29 of the bone 28. As indicated, the shortest length of the anchoring sleeve 1 extends over a distance indicated by the arrow 5.

Referring to FIGS. 1 and 2, the anchoring sleeve 1 is also provided with a plurality of longitudinal ribs 7 on the conical outer surface 2 for penetrating into the bone 28 in order to prevent rotation of the anchoring sleeve 1 therein. Each rib 7 has a cutting edge 10 extending longitudinally of the rib 7 with side faces 9 disposed in planes which intersect over an angle 8. In the direction 15 of loading, the side faces 9 terminate in a crosscut 12 which has side faces 11 and a knee at an angle 13. This allows the rib 7 to dig into the bone tissue 28 for effecting a primary anchorage and to resist turning of the sleeve 1. As indicated in FIG. 1, the ribs 7 may be equispaced over an angle 14 of 120° so that the sleeve 1 has three such ribs 7. Alternatively, the ribs 7 may lie closer together and may project less sharply.

Referring to FIG. 6, the clamp sleeve 20 is sized for insertion within the bore of the anchoring sleeve 1 and has a conical outer surface on an angle of taper 17 for frictionally engaging with the inner surface 3 of the anchoring sleeve 1. In this respect, the conical surface of the clamp sleeve 20 is disposed on an angle of taper of the order of magnitude of 10°. In addition, both the outer surface of the clamp sleeve 20 and the inner surface 3 of the anchoring sleeve 1 are roughened in order to effect a self-locking fit of the sleeves 1, 20 upon sliding of the sleeves into one another under prestress.

Figure 3:
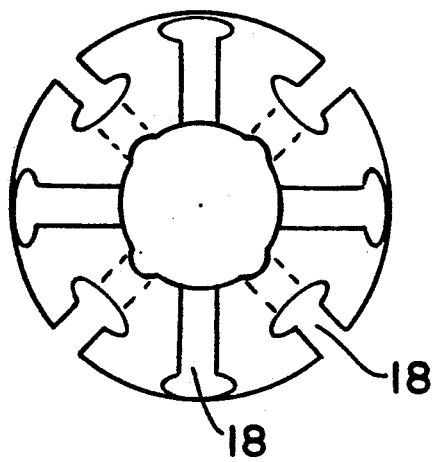
FIG. 3 illustrates an end view of a clamp sleeve constructed in accordance with the invention from an enlarged end.

As shown in FIG. 6, the clamp sleeve 20 is slotted so as to be deformable radially to a smaller inner diameter. To this end, the clamp sleeve 20 has a plurality of oppositely directed and circumferentially spaced slots 18 (see FIG. 3) which define a plurality of segments 25 therebetween to permit the sleeve 20 to be radially deformed. These slots 18 start alternately at the end faces of the clamp sleeve 20 and, at the opposite end face, leave only a small residual cross-section 26 in the clamp sleeve 20. Further, the bottom of each slot 18 has a rounding 19 which allows a narrowing of the slot during radial reduction of the diameter of the clamp sleeve 20.

Figure 7:
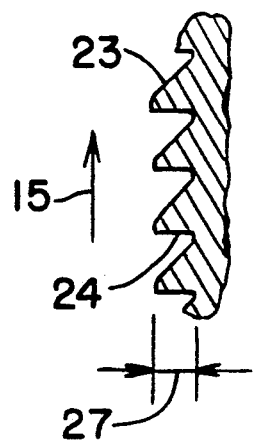
FIG. 7 illustrates an enlarged part cross-sectional view of a toothed segment of the clamp sleeve in accordance with the invention.
Figure 5:
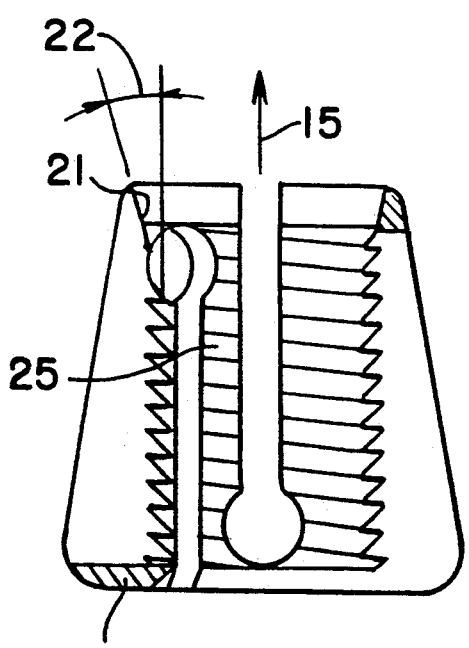
FIG. 5 illustrates a view taken on line V—V of FIG. 4.

Referring to FIG. 5, each segment 25 of the clamp sleeve is in the form of a saw tooth segment for engaging with a ligament (not shown) passing through the clamp sleeve 20. In this respect, each segment 25 has a plurality of teeth for engaging in a received ligament. Further, as indicated in FIG. 7, each tooth 23 has a steep flank 24 directed towards the enlarged end of loading of the clamp sleeve 20, that is, in a direction opposite the direction 15 of loading of the clamp sleeve 20. In addition, each tooth is of a height 27 which is matched to a depth of penetration admissible in the ligament (not shown).

Referring to FIG. 5, the clamp sleeve 20 has a conically tapered entry 21 at the smaller end for passage of the ligament therethrough and then continues cylindrically for equal stress distribution. The angle of taper 22 (half-apex-angle) of the entry 21 takes into consideration the differences in diameter between an unstressed ligament and a stressed ligament.

Figure 4:
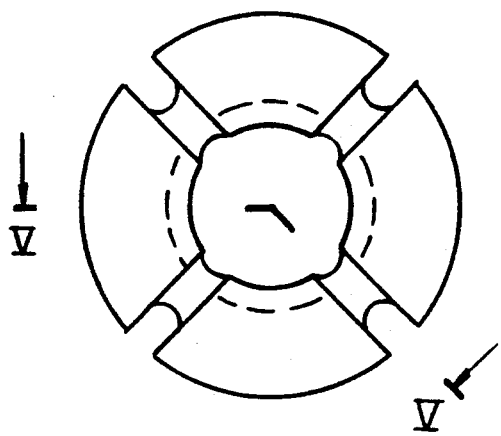
FIG. 4 illustrates an end view of the clamp sleeve from the smaller end.

As indicated in FIG. 4, the clamp sleeve 20 provides a clear opening through which a ligament may be initially passed.

Referring to FIG. 6, the clamp sleeve 20 is of an overall length indicated by the arrow 16 so as to be completely imbedded within the anchor sleeve 1, that is within the shortest length of the anchoring sleeve 1 as indicated by the arrow 5 in FIG. 2.

In use, the anchoring sleeve 1 is embedded in the opening in the bone 28 in suitable manner. Thereafter, the artificial ligament which is to be implanted is passed through the anchoring sleeve 1. At this time, the ligament is pulled outwardly under prestress against the direction 15 of loading and, at the same time, the clamp sleeve 20 which is also disposed on the ligament is pressed into the anchoring sleeve 1 in the direction 15 of loading until the saw tooth segments 25 embrace and hold the ligament so firmly that under the built-up pressure and the ligament tension in the direction 15 of loading, self-locking of the conical surfaces of the sleeves 1, 20 takes place.

Of note, upon pulling the ligament in against the direction 15 of loading, the ligament slides over the shallow backing-flanks 24 and rounded tips of the teeth 23.

During mounting of the clamp sleeve 20, the ligament may be brought to a predetermined tension, for example, by means of a spring balance. Thereafter, the clamp sleeve 20 may be pressed by a mounting tool into the anchoring sleeve 1 so that, with a reduction in the inner diameter, the saw tooth segments 25 press into the ligament and build up a prestress which leads to self locking of the conical surfaces of the sleeves 1, 20. This self locking remains after the removal of the mounting tool and with the later loading of the ligament still remains secure for a long time. A repetition of the mounting process or later re-stressing are possible as long as the anchored ligament projects far enough out of the clamp sleeve 20 for the ligament to be gripped and pulled back to overcome the self locking of the sleeves 1, 20 and in order to apply a predetermined prestress before pressing the clamp sleeve 20 in again.

The invention thus provides a ligament anchor of relatively simple construction. Further, the invention provides a ligament anchor which allows a ligament to be carefully fixed within a bone at a definite ligament tension.

What is claimed is:

1. A ligament anchor for fastening an artificial ligament in a bone, said anchor comprising
    an anchoring sleeve for insertion in a bone opening, said sleeve having a conical inner surface defining a bore extending therethrough; and
    a radially deformable clamp sleeve for insertion within said bore of said anchoring sleeve, said clamp sleeve having a conical outer surface for frictionally engaging with said conical inner surface of said anchoring sleeve and an inner surface having a plurality of inwardly facing saw tooth segments for engaging with a ligament passing through said clamp sleeve, each said segment having a plurality of teeth for engaging in a received ligament with each tooth having a steep flank directed towards an enlarged end of said clamp sleeve.

2. A ligament anchor as set forth in claim 1 wherein said segments are circumferentially spaced about said clamp sleeve and said teeth define segments of an internal screwthread.

3. A ligament anchor as set forth in claim 1 where each said surface is disposed on an angle of taper of the order of magnitude of 10° and is roughened to effect a self-locking fit with the other surface.

4. A ligament anchor as set forth in claim 1 wherein said clamp sleeve has a conically tapered entry at a smaller end for passage of a ligament therethrough.

5. A ligament anchor as set forth in claim 1 wherein said anchoring sleeve has a plurality of longitudinal ribs on a conical outer surface thereof for penetrating into a bone to prevent rotation of said anchoring sleeve therein.

6. A ligament anchor as set forth in claim 1 wherein said anchoring sleeve has an enlarged end having a bevel and wherein said clamp sleeve is of a longitudinal length to extend completely within said bevelled anchoring sleeve.

7. A ligament anchor comprising
    an anchoring sleeve for insertion in a bone opening, said sleeve having a conical outer surface tapering inwardly in a first direction and a conical inner surface defining a longitudinal bore; and a radically deformable clamp sleeve for insertion within said bore of said anchoring sleeve, said clamp sleeve having a conical outer surface for frictionally engaging with said conical inner surface of said anchoring sleeve and a plurality of oppositely directed circumferentially spaced slots defining a plurality of segments and permitting said clamp sleeve to be inwardly radially deformable, each said segment having a plurality of inwardly directed teeth formed on the inner surface for engaging in a ligament passing longitudinally through said clamp sleeve.

8. A ligament anchor as set forth in claim 7 wherein said clamp sleeve defines a cylindrical bore for receiving a ligament therein and a conically tapered entry into said bore.

9. A ligament anchor as set forth in claim 7 wherein each said surface is disposed on an angle of taper of the order of magnitude of a 10° and is roughened to effect a self-locking fit with the other surface.

10. A ligament anchor as set forth in claim 7 wherein said anchoring sleeve has an enlarged end having a bevel and wherein said clamp sleeve is of a longitudinal length to extend completely within said bevelled anchoring sleeve.

11. A ligament anchor as set forth in claim 7 wherein said anchoring sleeve has a plurality of longitudinal ribs on said outer surface for penetrating into a bone to prevent rotation of said sleeve therein.

* * * * *